United States Patent
Chappius

(10) Patent No.: US 6,565,572 B2
(45) Date of Patent: May 20, 2003

(54) FENESTRATED SURGICAL SCREW AND METHOD

(75) Inventor: James L. Chappius, Marietta, GA (US)

(73) Assignee: SDGI Holdings, Inc., Wilmington, DE (US)

( * ) Notice: Subject to any disclaimer, the term of this patent is extended or adjusted under 35 U.S.C. 154(b) by 75 days.

(21) Appl. No.: 09/746,668

(22) Filed: Dec. 20, 2000

(65) Prior Publication Data

US 2001/0021852 A1 Sep. 13, 2001

Related U.S. Application Data

(63) Continuation-in-part of application No. 09/545,920, filed on Apr. 10, 2000.

(51) Int. Cl.[7] .............................................. A61B 17/70
(52) U.S. Cl. ............................. 606/73; 606/61; 606/93
(58) Field of Search ............................. 606/60, 61, 65, 606/73, 92, 93, 94; 623/17.11, 17.16

(56) References Cited

U.S. PATENT DOCUMENTS

| 4,760,844 | A | * | 8/1988 | Kyle | 606/102 |
| 5,047,030 | A |   | 9/1991 | Draenert | 606/65 |
| 5,871,484 | A |   | 2/1999 | Spievack et al. | 606/60 |
| 5,971,987 | A |   | 10/1999 | Huxel et al. | 606/73 |
| 6,214,012 | B1 | * | 4/2001 | Karpman et al. | 606/61 |

FOREIGN PATENT DOCUMENTS

| EP | 0490517 A1 | 6/1992 |
| GB | 2157177 A | 10/1985 |
| JP | 07051292 | 2/1995 |
| JP | 07222752 | 8/1995 |
| JP | 09149906 | 6/1997 |
| JP | 10211213 | 8/1998 |

OTHER PUBLICATIONS

Brodie E. McKoy and Yuehuei H. An, "An Injectable Cementing Screw for Fixation in Osteoporotic Bone", pp. 216–220.

* cited by examiner

Primary Examiner—Cary E. O'Connor
(74) Attorney, Agent, or Firm—Woodard, Emhardt, Naughton, Moriarty & McNett LLP

(57) ABSTRACT

A preferred surgical anchor includes an elongated body with a proximal end and a distal end, a passage extending at least partially through the body from the proximal end, and at least one hole extending at least partially through the body that communicates with the passage. The passage and the at least one hole are configured so that a material is receivable in the passage, preferably, at the proximal end of the elongated body. So configured, the material may be delivered through the passage, through the at least one hole, and into the skeletal member. Additionally, a cutting member preferably is arranged at the distal end of the elongated body, with the cutting member being configured to enable penetration of the at least a portion of the elongated body into the skeletal member. Systems and methods also are provided.

10 Claims, 3 Drawing Sheets

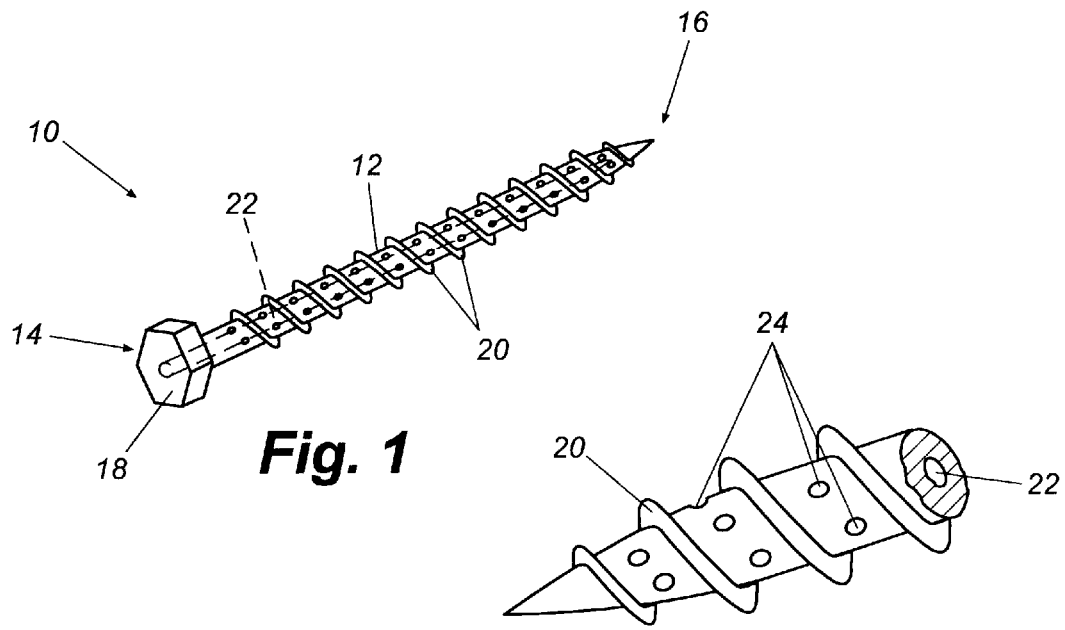
Fig. 1
Fig. 2
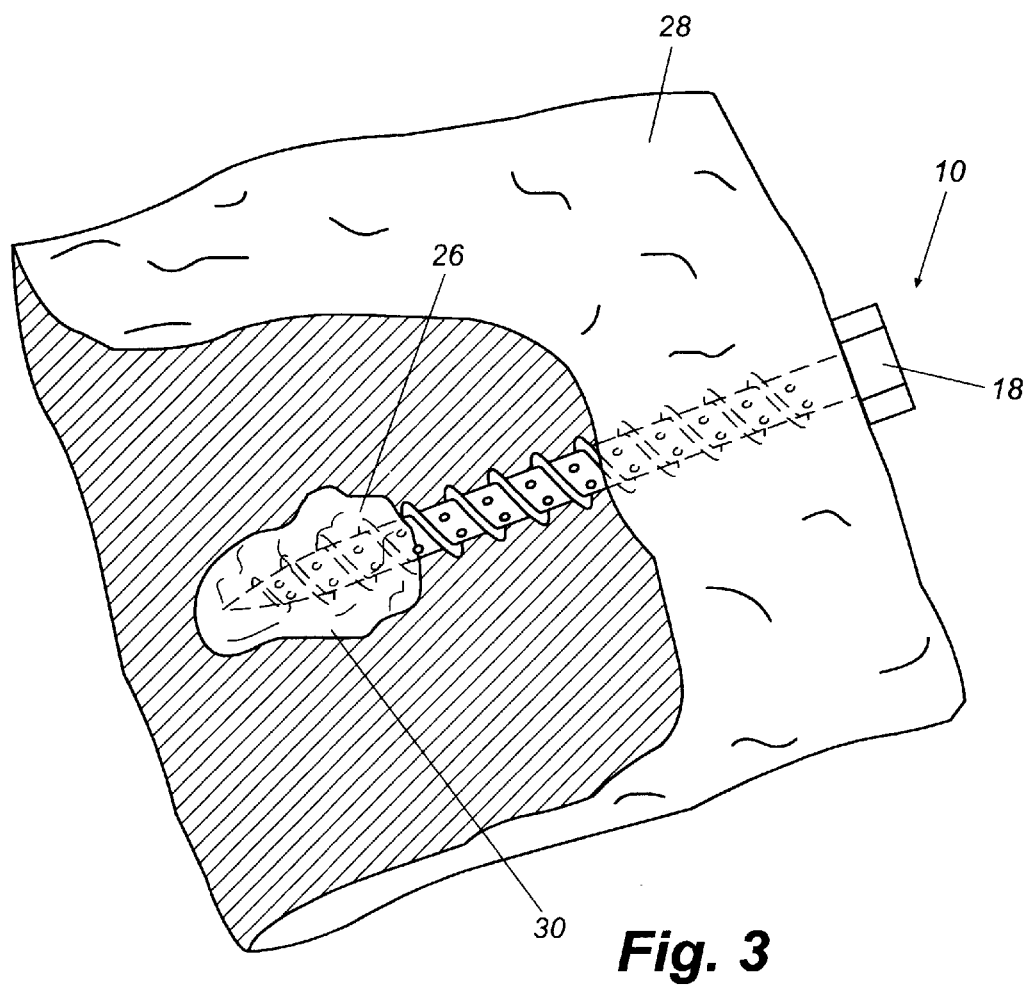
Fig. 3

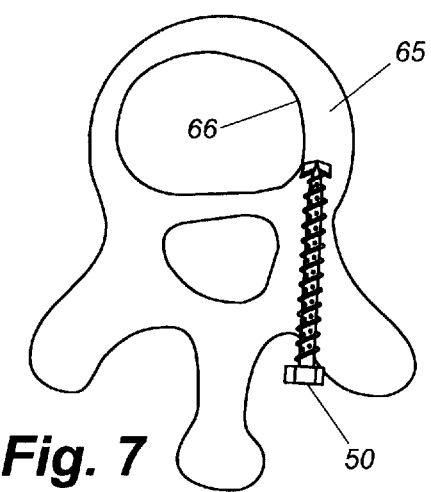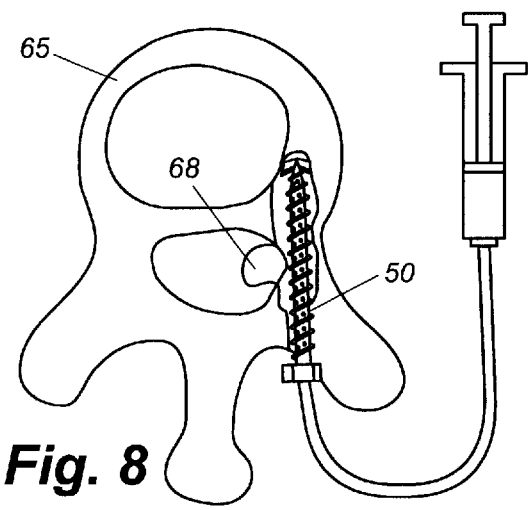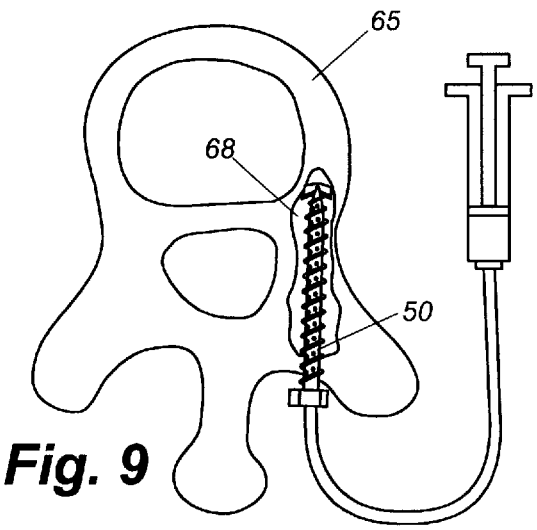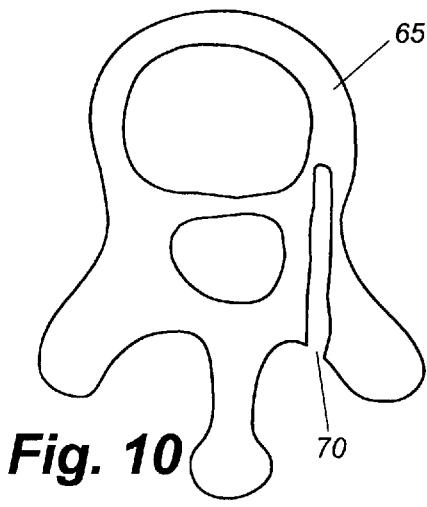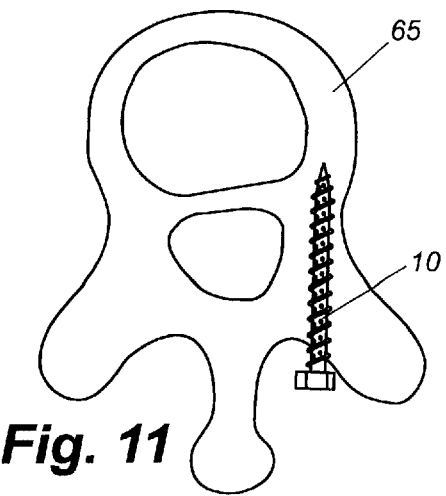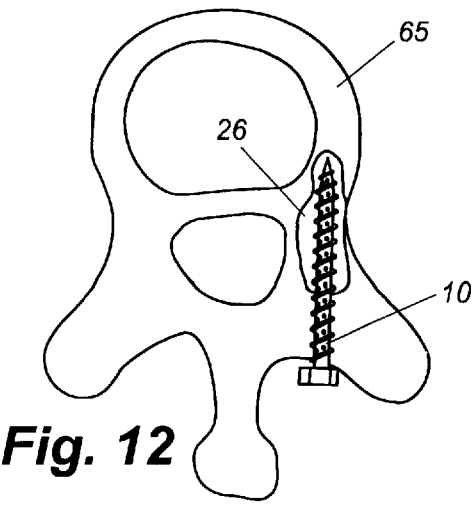

FENESTRATED SURGICAL SCREW AND METHOD

CROSS REFERENCE TO RELATED APPLICATIONS

This application is a Continuation-In-Part application which is based on and claims priority to U.S. patent application Ser. No. 09/545,920, filed on Apr. 10, 2000, pending.

BACKGROUND OF THE INVENTION

1. Field of the Invention

The present invention generally relates to surgical instruments and, in particular, relates to surgical screws which are adapted for use with skeletal members, such as vertebrae, for example, and methods for their use.

2. Description of Related Art

Skeletal structures are formed of bones and adjoining structures which include cartilage, for instance. For various reasons, these skeletal structures may require artificial support or stabilization. For example, the human spine is composed of a column of thirty-three bones, called vertebrae, and their adjoining structures. The twenty-four vertebrae nearest the head are separate bones capable of individual movement and generally are connected by anterior and posterior longitudinal ligaments and by discs of fibrocartilage, called intervertbral discs, positioned between opposing faces of adjacent vertebrae. Each of these vertebrae include a vertebral body and a dorsal arch that enclose an opening, called the vertebral foramen, through which the spinal cord and spinal nerves pass. The remaining nine vertebrae are fused to form the sacrum and the coccyx and are incapable of individual movement.

It is well known in the prior art to utilize pedicle screws for posterior lumbar stabilization procedures. These procedures typically include inserting a pedicle screw posteriorly into the pedicle or pillar of the lumbar spine, and then connecting the screw to either plates or rods for stabilization of the lumbar spine for fractures, tumors and various degenerative conditions. A bone graft also can be added to help solidify the stabilization. When this procedure is used on osteoporotic patients, however, pedicle screw fixation is sometimes difficult to achieve because the threads of the pedicle screw are unable to properly secure within the material of the pillar.

Similar results also may be observed when attempting to secure surgical anchors within the material of other skeletal members.

An additional concern relates to the potential of violating the vertebral foramen while attempting to secure a surgical anchor within the material of a pillar.

Therefore, there exists a need for improved surgical screws which address these and other shortcomings of the prior art.

SUMMARY OF THE INVENTION

Briefly described, the present invention relates to surgical screws or anchors which are adapted for use with skeletal members. In a preferred embodiment, the surgical anchor includes an elongated body with a proximal end and a distal end, a passage extending at least partially through the body from the proximal end, and at least one hole extending at least partially through the body that communicates with the passage. The passage and the at least one hole are configured so that a material is receivable in the passage, preferably, at the proximal end of the elongated body. So configured, the material may be delivered through the passage, through the at least one hole, and into the skeletal member. Additionally, a cutting member preferably is arranged at the distal end of the elongated body, with the cutting member being configured to enable penetration of the at least a portion of the elongated body into the skeletal member.

Embodiments of the present invention also may be construed as providing methods for inserting an anchor into a skeletal member. In this regard, a preferred embodiment includes the steps of: (1) providing a first anchor having a proximal end, a distal end, and a cutting member, the cutting member being configured to enable penetration of the distal end into the skeletal member; (2) inserting the first anchor into the skeletal member to form an anchor-receiving hole; (3) checking for a violation of a wall of the skeletal member; (4) removing the first anchor from the skeletal member; and (5) inserting a second anchor into the anchor-receiving hole.

Other embodiments of the present invention may be construed as providing systems for lumbar spine stabilization. In this regard, a preferred embodiments includes a plurality of first anchors, with each of the first anchors incorporating a proximal end, a distal end, a cutting member, a passage, and at least one hole. Each of the cutting members is configured to enable penetration of the distal end of its respective anchor into a skeletal member so that an anchor-receiving hole is formed in the skeletal member. A plurality of second anchors also are provided, with each of the second anchors incorporating a proximal end, a distal end, a passage, and at least one hole.

Other features and advantages of the present invention will become apparent to one with skill in the art upon examination of the following drawings and detailed description. It is intended that all such additional features and advantages be included herein within the scope of the present invention, as defined by the claims.

BRIEF DESCRIPTION OF THE SEVERAL VIEWS OF THE DRAWINGS

The present invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 1 is a perspective view of a preferred embodiment of the present invention;

FIG. 2 is a cut-away perspective view of the embodiment of FIG. 1, showing detail of the material dispersion holes;

FIG. 3 is a partially cut-away perspective view of the embodiment of FIGS. 1 and 2 shown anchored within a representative skeletal member.

FIG. 7 is a schematic view of an anchor of the present invention inserted in a representative vertebrae.

FIG. 8 is a schematic view of a vertebrae with a violated pedicle wall, showing detail of a representative method for determining the violation.

FIG. 9 is a schematic view of a vertebrae without a violated pedicle wall, showing detail of a representative method for determining a violation.

FIG. 10 is a schematic view of the vertebrae of FIG. 9 with the anchor removed, thereby exposing an anchor-receiving hole.

FIG. 11 is a schematic view of the vertebrae of FIG. 10 shown with an anchor being inserted into the anchor-receiving hole.

FIG. 12 is a schematic view of the vertebrae of FIG. 10 with a material having been applied to the vertebrae via the anchor.

DETAILED DESCRIPTION OF THE INVENTION

Figure 4:
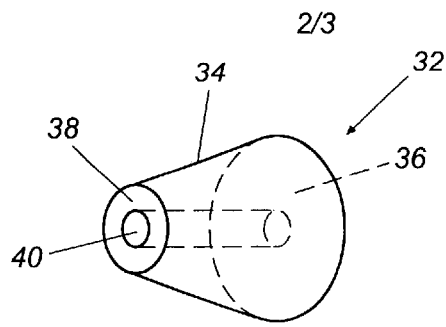
FIG. 4 is a perspective view of a preferred embodiment of a plug utilized in preferred embodiments of the present invention.

Reference will now be made in detail to the description of the present invention as illustrated in the drawings with like numerals indicating like parts throughout the several views. As shown in FIGS. 1 and 2, a preferred embodiment of the anchor 10 of the present invention incorporates an elongated body 12, which preferably is cylindrical in shape (although various other shapes may be utilized), with a proximal end 14 and a distal end 16. Preferably, the anchor is formed of a relatively non-reactive, durable material, such as stainless steel, titanium, etc. Although not necessary, distal end 16 preferably includes an anchor head 18, formed in a conventional hexagonal configuration, for instance, although various other configurations may be utilized and are considered well within the scope of the present invention, thereby allowing the anchor 10 to be conveniently driven into material of a skeletal member with the use of a driving tool (not shown), such as a screw driver, wrench, or drill incorporating a anchor-driving adapter, among others. In other embodiments, i.e., embodiments not incorporating external threads, for example (as described hereinafter), driving of the anchor may be accomplished with an impact tool, such as a mallet, impact wrench, etc.

Additionally, some embodiments of the body 12 include external threads 20, preferably formed along substantially the entirety of its length, although, in some embodiments, the external threads may be provided on less than substantially the entirety of the length of the anchor depending upon the particular application. In still other embodiments, no external threads are provided, although various other protrusions, ridges, or other friction-enhancing features and/or surface treatments may be provided on the exterior of the anchor to facilitate secure engagement of the anchor within a skeletal member.

Body 12 also incorporates a passage 22 formed at least partially therethrough which preferably extends into the body from proximal end 14. In some embodiments, the passage 22 may be configured as a longitudinal bore, for instance. Passage 22 communicates with one or more fenestrations or dispersion holes 24, preferably formed at distal end 16, which are adapted for dispersing medical adhesive or boding cement 26 (e.g., polymethylmethacrylate (PMMA), cranioplast, etc.), bone healing substances, such as bone morphogenic protein, among others, from the anchor.

Since cement 26 may produce an exothermic reaction during curing, holes 24 preferably are formed in the distal one-third of the anchor in order to reduce the possibility of thermal injury to nerve roots in the vicinity of the anchor. However, in embodiments utilizing non-exothermic reacting cement, the holes may be formed at various locations along the length of the anchor for dispersing the cement, as required, based upon the needs of the particular application.

As shown in FIG. 3, a preferred embodiment of anchor 10 is configured to be driven into a skeletal member, such as vertebral body 28. Depending upon the particular application, the skeletal member may be pre-drilled, thereby forming a anchor-receiving hole into which the anchor may be driven (a preferred method for pre-drilling is described in detail hereinafter). Driving of the anchor may be accomplished in any suitable manner, including driving with the use of a driving tool as described hereinbefore. Preferably, after the anchor has been at least partially driven within the skeletal member, cement 26 is then delivered into passage 22, such as by injecting the cement with a syringe or other suitable delivery device, so that at least some of the cement is delivered through the passage 22, through the hole(s) 24, and out of the anchor. As the cement 26 passes out of the anchor, the cement preferably engages the various pores, concavities and interstices of the vertebral body 28, thereby creating a mass or collection 30 of cement about the anchor, or more proximal in the pedicle or bone pillar. After curing, the cement creates a firm fixation or anchoring of the anchor in the vertebral body, pedicle or other bony structure(s).

Additionally, since the cement tends to engage the various pores, concavities and interstices of the skeletal member, the skeletal member may tend to be strengthened. Thus, the present invention has been found to be particularly useful for securely anchoring anchors within skeletal members of osteoporotic patients, for instance.

Figure 5:
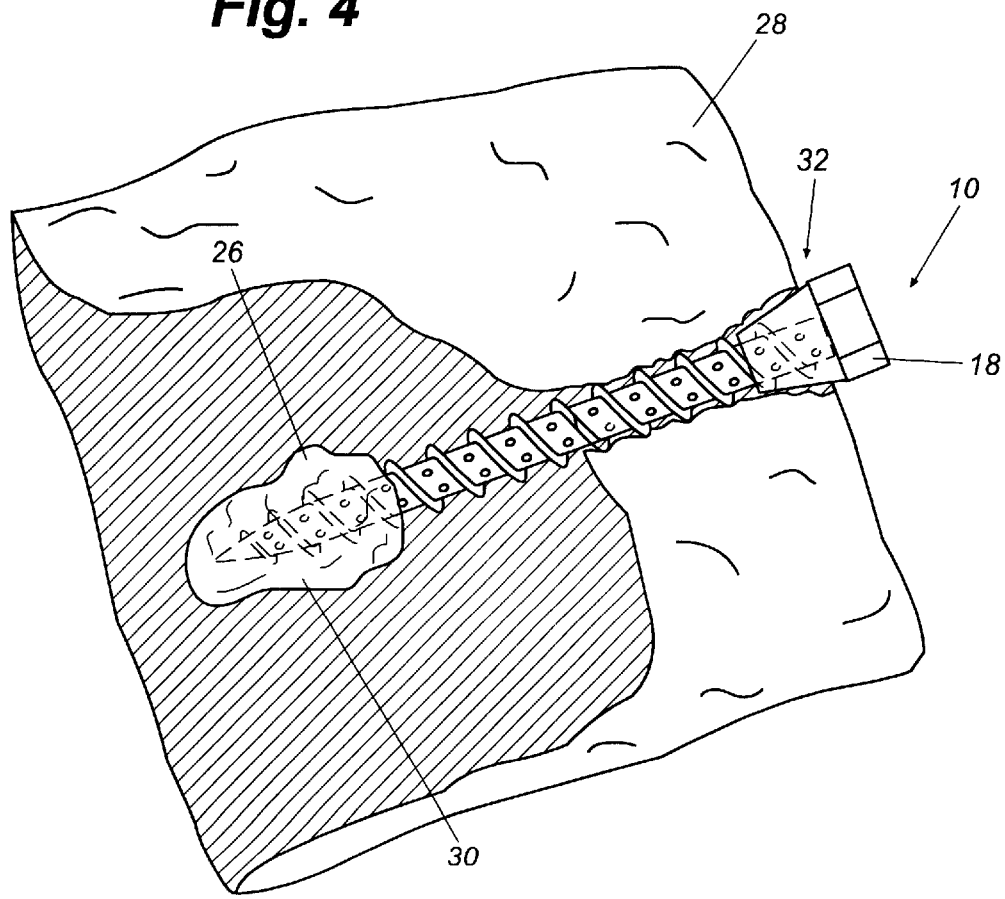
FIG. 5 is a partially cut-away perspective view of a preferred embodiment of the invention showed anchored within a representative skeletal member.

As depicted in FIG. 4, preferred embodiments of the anchor 10 may incorporate the use of a plug member 32 which is configured for securing the proximal end of the body 12 within a skeletal member. Preferably, plug member 32 is formed of a plastic or other semi-compliant material which may cooperate with the material of a skeletal member to substantially fix the position of the proximal end of the body within the skeletal member; this would act as a shim to make fixation more secure, especially when bone cement in the pedicle would be contraindicated. Preferably, plug 32 incorporates a tapered side wall 34 which extends outwardly and downwardly from a first end wall 36 to a second end wall 38. Additionally, the plug member preferably incorporates a bore 40 extending through the first and second end walls that is sized and shaped to receive the body 12 of an anchor therethrough. So configured, plug member 32 may be received about the body of an anchor, with the anchor then being insertable into a skeletal member 28, such as depicted in FIG. 5. So positioned, the plug member 32 preferably engages the skeletal member at the proximal end of the anchor 10, thereby substantially preventing movement of the proximal end of the anchor relative to the skeletal member.

Figure 6:
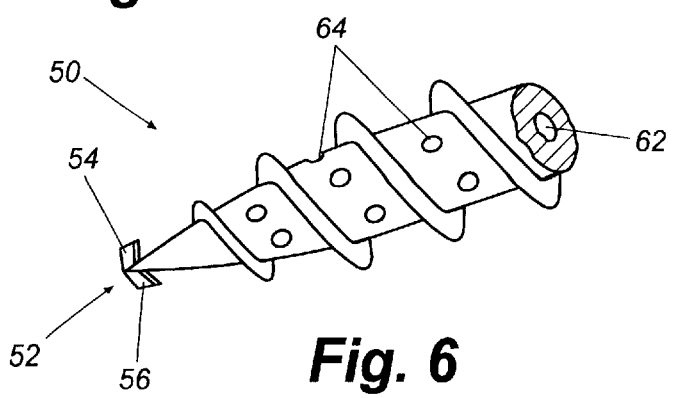
FIG. 6 is a cut-away perspective view of an alternative embodiment of the present invention.

As mentioned hereinbefore, depending upon the particular application, the skeletal member may be pre-drilled for forming a anchor-receiving hole into which a suitable anchor may be driven. In this regard, reference is made to FIG. 6 which depicts an alternative embodiment of the anchor 50, which is adapted for drilling an anchor-receiving hole. More specifically, anchor 50 incorporates a cutting member 52, which preferable is disposed at the distal end of the anchor. In the embodiment depicted in FIG. 6, cutting member 52 includes blades 54 and 56 which extend radially outwardly from a longitudinal axes if the anchor. The blades are formed of a suitably hard material and are appropriately shaped for forming an anchor-receiving hole within a skeletal member as the anchor is turned. So provided, (as depicted in FIG. 7), anchor 50 may be appropriately embedded within a skeletal member 65, such as a vertebrae, and then may be removed, e.g., by unscrewing the anchor, thereby exposing an anchor-receiving hole within the skeletal member.

In some embodiments, the anchor 50 may incorporate a passage 62, formed at least partially therethrough. The passage 62 may be configured as a longitudinal bore, for example, and communicates with one or more fenestrations or dispersion holes 64, which are adapted for dispersing medical adhesive or boding cement (e.g., PMMA, cranioplast, etc.), bone healing substances, such as bone morphogenic protein, among others, from the anchor.

As mentioned briefly hereinbefore, placing an anchor within a skeletal member, such as a vertebrae, may cause a violation of the skeletal member or a portion thereof, such as a violation of a pedicle wall 66, for example. In particular, when inserting an anchor into a vertebrae, the anchor may protrude through or, otherwise, damage the pedicle wall, thereby potentially exposing the spinal column (and nerve roots) to various materials that are intended to be injected into the anchor. Inserting an anchor into a vertebrae also may cause the anchor to protrude through or, otherwise, violate the neuro-foramin.

In order to reduce the potential for damage and/or injury, once anchor 50 has been appropriately embedded within a skeletal member, e.g., a vertebrae (as shown in FIG. 8), a material 68, such as a radiopaque dye, among others, may be injected into the anchor. So provided, the dye may be forced through the anchor, out through the various holes of the anchor, and into the surrounding bone and tissue. Penetration of the dye may then be evaluated and a determination may be made as to whether the anchor has violated the pedicle wall, e.g., determine whether the dye has penetrated one or more areas adjacent the pedicle wall, thereby indicating a violation. For instance, FIG. 8 depicts a skeletal member violation (dye penetration into the spinal column), whereas FIG. 9 depicts non-violation of a skeletal member (no extravasation of the injected dye outside the bone).

If a violation of the pedicle wall is indicated, anchor 50 may be removed, and an anchor may be embedded within the vertebrae at a different orientation and/or location. The aforementioned process of injecting dye and inspecting for a pedicle wall violation may then be repeated as required.

Once a suitable anchor-receiving hole 70 has been formed by inserting the anchor 50, the anchor may be removed, such as depicted in FIG. 10. As depicted in FIG. 11, a pedicle screw or anchor, such as anchor 10 (FIG. 1), may be appropriately anchored within the anchor-receiving hole, and, as depicted in FIG. 12, material 26, such as cement, and/or bone healing compounds may be injected into the anchor. It should be noted that various modifications to the aforementioned procedure may be utilized, including, but not limited to, anchoring the anchor 50 into the skeletal member by injecting cement therethrough.

The foregoing description has been presented for purposes of illustration and description. It is not intended to be exhaustive or to limit the invention to the precise forms disclosed. Modifications or variations are possible in light of the above teachings. The embodiment discussed, however, was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly and legally entitled.

What is claimed is:

1. A method for inserting an anchor into a vertebral body, said method comprising the steps of:

providing a first anchor having a proximal end, a distal end, and a cutting member, said cutting member being configured to enable penetration of the distal end into the vertebral body, said first anchor having a longitudinal passage formed at least partially therethrough and at least one hole transversely communicating with said longitudinal passage;

inserting the first anchor at least partially into the pedicle region of the vertebral body to form an anchor-receiving hole such that the at least one hole is at least partially disposed within the vertebral body; and checking for a transverse violation of a wall of the vertebral body, comprising:
  dispensing a material through the passage and the at least one hole of the first anchor and into the vertebral body; and
  determining whether the material disperses transversely beyond a predetermined portion of the vertebral body.

2. The method of claim 1, wherein if the material disperses beyond the predetermined portion of the vertebral body:
  removing the first anchor from the anchor-receiving hole;
  re-inserting the first anchor into the pedicle region of the vertebral body to form another anchor-receiving hole; and
  re-checking for a violation of a wall of the vertebral body.

3. The method of claim 1, wherein said material is a radiopaque dye.

4. A system for inserting an anchor into a skeletal member, comprising:
  an anchor body having a proximal end portion and a distal end portion, said distal end portion being configured to enable penetration into the skeletal member;
  a passage extending from said proximal end portion and at least partially through said anchor body;
  at least one hole extending at least partially through said anchor body and communicating with said passage; and
  a dye deliverable through said passage, out said at least one hole, and into surrounding tissue of the skeletal member; and
  wherein said anchor body is removable from said skeletal member to provide an anchor-receiving opening in the skeletal member with a second anchor insertable into said anchor-receiving opening in the skeletal member, said second anchor including an anchor body having a proximal end portion and a distal end portion, a passage extending from said proximal end portion and at least partially through said anchor body, and at least one hole extending at least partially through said anchor body and communicating with said passage.

5. The system of claim 4, wherein said distal end portion of said anchor body is self-drilling to enable formation of an anchor-receiving opening in the skeletal member.

6. The system of claim 4, wherein said dye is radiopaque.

7. The system of claim 4, further comprising bonding cement deliverable through said passage, out said at least one hole, and into surrounding tissue of the skeletal member.

8. The system of claim 4, further comprising bonding cement deliverable through said passage of said second anchor, out said at least one hole of said second anchor, and into surrounding tissue of the skeletal member.

9. A method for inserting an anchor into a skeletal member, said method comprising the steps of:

providing a first anchor having a proximal end, a distal end, and a cutting member, said cutting member being configured to enable penetration of the distal end into the skeletal member;

inserting the first anchor into the skeletal member to form an anchor-receiving hole;

checking for a violation of a wall of the skeletal member;

removing the first anchor from the skeletal member; and inserting a second anchor into the anchor-receiving hole.

10. The method of claim 9, wherein said second anchor has a passage formed therethrough, and at least one hole communicating with said passage, and further comprising:

delivering bonding cement into the passage of the second anchor such that at least a portion of the cement is delivered from said passage, through said at least one hole, and into the skeletal member for anchoring the second anchor within the skeletal member.

* * * * *